United States Patent [19]
Walus et al.

[11] Patent Number: 5,575,794
[45] Date of Patent: Nov. 19, 1996

[54] TOOL FOR IMPLANTING A FIDUCIAL MARKER

[76] Inventors: Richard L. Walus, 69 Trout Farm La., Duxbury, Mass. 02332; Jennifer J. McCrory, 9 Timberland Dr., Lincoln, R.I. 02865; John A. Santangelo, 16 Rounsevell Dr., East Freetown, Mass. 02717; Raphael Meloul, 340 Grove St., Randolf, Mass. 02368

[21] Appl. No.: 186,946

[22] Filed: Jan. 27, 1994

Related U.S. Application Data

[63] Continuation-in-part of Ser. No. 17,167, Feb. 12, 1973, abandoned.

[51] Int. Cl.⁶ .......................... A61B 17/00; A61B 17/90; A61B 17/17
[52] U.S. Cl. ..................... 606/116; 606/96; 606/167; 606/185; 606/130; 403/293; 403/326
[58] Field of Search .................. 606/79, 80, 96, 606/98, 116, 167, 180, 185, 60, 130; 403/293, 292, 326

[56] References Cited

U.S. PATENT DOCUMENTS

| | | | |
|---|---|---|---|
| 2,294,303 | 8/1942 | Jagow | 77/55 |
| 2,525,669 | 10/1950 | Hainault . | |
| 3,074,407 | 1/1963 | Moon et al. . | |
| 3,128,768 | 4/1964 | Geistauts . | |
| 3,867,932 | 2/1975 | Huene | 606/80 |
| 3,892,232 | 7/1975 | Neufeld . | |
| 4,298,024 | 11/1981 | McLeod | 137/624.11 |
| 4,341,206 | 7/1982 | Perrett et al. . | |
| 4,549,538 | 10/1985 | Schadrack et al. . | |
| 4,613,324 | 9/1986 | Ghajar | 604/49 |
| 4,618,978 | 10/1986 | Cosman | 378/164 |
| 4,798,213 | 1/1989 | Doppelt | 128/754 |
| 4,821,716 | 4/1989 | Ghajar et al. . | |
| 4,826,487 | 5/1989 | Winter | 604/175 |
| 4,840,291 | 6/1989 | Merlin | 403/326 |
| 4,896,663 | 1/1990 | Vandewalls | 606/79 |
| 4,903,692 | 2/1990 | Reese | 606/99 |
| 4,931,056 | 6/1990 | Ghajar et al. | 606/130 |
| 4,947,871 | 8/1990 | Grieshaber | 128/898 |
| 4,957,505 | 9/1990 | McDonald | 623/6 |
| 4,963,144 | 10/1990 | Huene | 606/73 |
| 4,991,579 | 2/1991 | Allen | 128/653 |
| 4,998,938 | 3/1991 | Ghajar | 606/130 |
| 5,071,420 | 12/1991 | Paulos et al. | 606/99 |
| 5,135,531 | 8/1992 | Shiber | 606/159 |
| 5,172,702 | 12/1992 | Leigh et al. | 128/754 |
| 5,312,354 | 5/1994 | Allen et al. | 606/167 |
| 5,380,336 | 1/1995 | Misko et al. | 606/130 |

FOREIGN PATENT DOCUMENTS

| | | |
|---|---|---|
| WO88/02246 | 7/1985 | European Pat. Off. . |
| 0427358 | 5/1991 | European Pat. Off. . |

Primary Examiner—Michael Powell Buiz
Assistant Examiner—Scott B. Markow
Attorney, Agent, or Firm—Kenyon & Kenyon

[57] ABSTRACT

The present invention provides a tool for inserting a fiducial marker. It comprises a housing and guide assembly, an obturator assembly, a drill for forming a bore hole at an implantation site, and a marker inserter for inserting a marker into the bore hole. The housing and guide assembly comprise a cylindrical housing having a bore provided therein, and a guide tube that is disposed and shiftable within the bore of the housing. The obturator assembly, drill and marker inserter are insertable in the distal end of the guide tube and shiftable therein.

40 Claims, 13 Drawing Sheets

TOOL FOR IMPLANTING A FIDUCIAL MARKER

This application is a continuation-in-part of application Ser. No. 08/017,167 filed Feb. 12, 1993 now abandoned.

BACKGROUND OF THE INVENTION

The present invention relates to a method and apparatus for implanting a fiducial marker. More specifically, the invention relates to an apparatus and method that provide for the creation of a hole that does not penetrate the entire thickness of a segment of bone, and which is sized to accommodate a fiducial marker. The invention also provides for the insertion of an imaging marker or marker base into the hole so created.

Recent years have seen the development of diagnostic techniques that allow the practicing clinician to obtain high fidelity views of the anatomical structure of the human body. Imaging systems such as computed tomographic (CT) x-ray imagers, positron emission tomographic (PET) scanners, single photon emission computed tomography (SPECT) scanners and nuclear magnetic resonance imaging (MRI) machines have provided clinicians with the ability to improve visualization of the anatomical structure of the human body without surgery or other invasive techniques. In lieu of exploratory surgery, the patient can be scanned by such imaging systems, and the patient's anatomical structure can be reproduced in a form for evaluation by a trained doctor. A problem associated with such scanning techniques concerns the accurate selection and comparison of views of identical areas in images that have been obtained by imagers at different times or by images obtained essentially at the same time using different image modalities, e.g., CT, MRI, SPECT, and PET. This problem has two aspects. First, in order to relate the information in an image of the anatomy to the anatomy itself, it is necessary to establish a one-to-one mapping between points in the image and points of anatomy. This is referred to as registering image space to physical space.

The second aspect concerns the registration of one image space onto another image space. The goal of registering two arbitrarily oriented three dimensional images is to align the coordinate systems of the two images such that any given point in the scanned anatomy is assigned identical addresses in both images. The calculation of the rigid body transformation necessary to register the two coordinate systems requires knowledge of the coordinate vectors of at least three points in the two systems. Such points are called "fiducial points" or "fiducials," and the fiducials used are the geometric centers of markers, which are called "fiducial markers". These fiducials are used to correlate image space to physical space and to correlate one image space to another image space. The fiducial markers provide a constant frame of reference visible in a given imaging mode to make registration possible.

The general technique for using fiducial markers to obtain registration of image data is set forth in U.S. Pat. No. 4,991,579 and U.S. Pat. No. 5,142,930, the contents of both of which are incorporated herein by reference. Briefly, these patents teach implanting within a patient a series of at least three fiducial markers whose location can be determined in the image space of an imager.

Broadly speaking, image markers can be either temporary or permanent with respect to the duration of their placement within the human body. Permanent markers are unitary in construction, and are placed entirely beneath the epidermis of the skin for extended periods of time. Temporary markers have two parts: a base that is implanted into bone, and a temporary image marker portion that is attached to the base for brief intervals of time. In the temporary marker, the image marker portion protrudes from the skin.

In both the temporary and the permanent markers, the marker portion may take the form of a hollow container that is charged with aqueous imaging agents to provide imaging capability in the desired imaging modality or modalities. Patent application Ser. No. 08/017,167 (the contents of which are incorporated herein by reference) more fully discusses the structure of each type of marker and the imaging agents which can be used therewith.

Whichever type of marker is employed, it is necessary for the clinician to implant the marker into some solid, dimensionally stable portion of the anatomy. The preferred location for the placement of fiducial markers is bone, as it is generally dimensionally stable, and can provide a secure anchor site for a fiducial marker. The placement of a fiducial marker into bone requires that a hole be drilled for the fiducial marker.

Permanent fiducial markers typically are implanted in their entirety in bone tissue beneath the skin; temporary markers (as noted above) have distinct base and marker portions, with respect to which only a portion of the base need be implanted into bone. One method for implanting a fiducial marker is described in U.S. Pat. No. 5,178,164, which is incorporated herein by reference. According to this method, a marker is screwed into bone tissue under force. A hex-key like wrench engages a socket on the upper surface of the marker to provide the necessary drive connection between the two elements.

Numerous surgical tools have been developed to facilitate the insertion of foreign objects into the human body. Recent years, in particular, have seen the development of very specialized tools for many surgical procedures so as to minimize the invasiveness of the procedure in question. One such specialized tool is an apparatus for the insertion of a catheter into the ventricular portion of the brain, and is set forth in U.S. Pat. No. 4,931,056, which is incorporated herein by reference. The patent discloses a catheter guide apparatus comprising a hand operated twist drill device, configured for insertion in a first tubular guide. A second guide, of reduced diameter relative to the first tubular guide, is insertable into the first guide upon completion of a through-hole in the skull and subsequent removal of the twist drill, to facilitate entry of a catheter into the ventricle portion of the brain.

There remains a need for a tool specialized to facilitate the creation of a hole that is configured to accommodate a fiducial marker. There further remains a need for a tool that can quickly be reconfigured to facilitate the secure insertion of a fiducial marker into the hole so created. There further remains a need for a tool especially adapted for the insertion of a fiducial marker into bone tissue that is simple to use, minimally invasive, and which includes safety features to prevent the formation of an unwanted through-hole in bone tissue.

SUMMARY OF THE INVENTION

The present invention provides a tool for first creating a hole of predetermined depth into bone tissue, and then inserting a fiducial marker into the hole in the bone. The tool uses a guide assembly and means that cooperate with the guide assembly for perforating the skin, securely siting the guide assembly, forming the bore hole, and inserting the marker.

Before using the tool, the physician first determines the site at which the fiducial marker is to be inserted and marks that site with an incision. The insertion tool is then placed over the incision. The tool provides a guide assembly that includes a housing that is shaped to provide a secure abutment with respect to a desired portion of the anatomy of a patient. The housing contains a bore which accommodates both a cylindrical metal cannula and a spring that is entrained between a ring on the cannula and a shoulder within the housing; the cannula is shiftable within the housing against a force supplied by this spring. One end of the cannula terminates in a row of sharp teeth for establishing a firm connection between the housing and the patient's tissue. The other end of the cannula is inserted within a handle having an opening that leads to the hollow cannula. The cannula is sized to accommodate a number of implements useful in establishing a hole of proper size and inserting a marker, including an obturator, a hand drill, and a specialized insertion tool. After the incision has been made, an obturator having a sharp tip at its proximal end is inserted into the cannula. The length of the obturator is sufficient for a length of it to protrude beyond the proximal end of the cannula so that its pointed tip can be brought into contact with the incision site. The initial positioning of the guide assembly is accomplished simply by a downward shifting of the housing and the guide assembly along the length of the obturator until the teeth of the cannula contact tissue. The housing is then axially shifted along the cannula against the spring entrained between the cannula and the housing, until the housing abuts the patient's skin.

Once the tool housing is properly sited, the obturator is removed from the cannula and a hand drill inserted in its place. The hand drill is used to make a hole of predetermined diameter and depth (the depth of the hole drilled is limited by the manner in which the geometry of the housing, drill bit and drill bit length cooperate with one another). The hand drill is then removed from the cannula.

The tool can be used to insert either the marker base of a temporary fiducial marker or a permanent, fully implantable fiducial marker. Where a temporary marker is to be installed, its base, which may have a polygonal socket, is attached to the end of an insertion tool that terminates in a drive element. The insertion tool and marker base are then inserted into the cannula. By pressing the fiducial marker base into the hole and then rotating the handle of the insertion tool, the marker base (which has a self-tapping thread) can be screwed into the hole formed by the hand drill. The insertion tool is then pulled away from the fiducial marker base and is removed from the cannula. The procedure for inserting a permanent fiducial marker is similar, differing chiefly in that instead of screwing in the marker, it is press-fitted into the hole. At this point the procedure is complete, and the guide assembly is removed from the patient.

BRIEF DESCRIPTION OF THE DRAWINGS

The present invention will now be described with reference to the accompanying figures, in which:

FIGS. 14A and 14B illustrate the use of an additional embodiment that employs a trocar instead of an obturator in a two-stage process.

DETAILED DESCRIPTION

Figure 1:
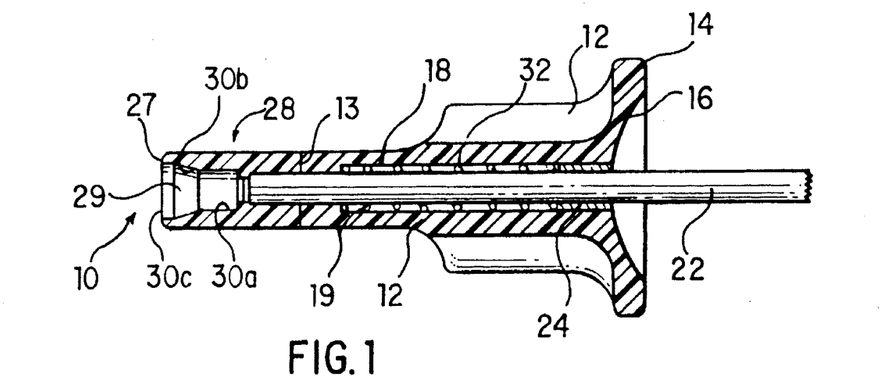
FIG. 1 is a cross-sectional view of the guide assembly.

Turning initially to FIG. 1, there is illustrated a guide assembly 10 of the present invention. The guide assembly 10 serves to provide a means for establishing and maintaining a geometrically constrained passageway with respect to the patient for the introduction of a drill for forming a hole. The guide assembly is subsequently used in a similar manner to receive a specialized tool for inserting a fiducial marker or marker base into the hole. The guide assembly is made up of two principal components which shall be discussed in turn: a guide housing 12, and a cannula guide tube subassembly 20.

The generally tubular guide housing 12, which may be made of plastic, has an inner bore 18 running along the longitudinal axis of the guide housing. The bore begins at the distal annular surface 13 of the guide housing 12 and continues a distance before increasing in diameter at shoulder 19. At the proximal end of the guide housing 12, the walls of the housing flare outward in a perpendicular direction away from the axis of the cylinder to form a base 14. The base 14 is scalloped in shape, forming a concave depression 16.

Figure 2:
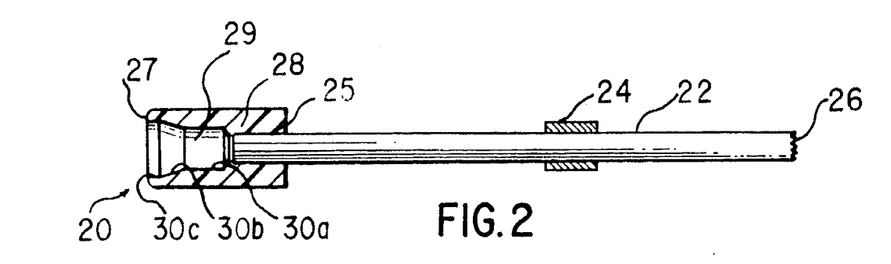
FIG. 2 shows the cannula guide tube subassembly, partially in section.

Fitted into the guide assembly 10 is a cannula guide tube subassembly 20 (see FIG. 2). This subassembly consists of a stainless steel metal cannula guide tube 22 that fits within the bore 18 of the housing 12. The cannula guide tube 22 is hollow, and terminates at its proximal end in a row of sharp teeth 26. The function of these teeth is to help provide a secure connection between the guide assembly and the tissue of the patient so as to prevent shifting of the housing and guide assembly during drilling and insertion of the marker. At its distal end, the cannula guide tube 22 is fitted to the bore of a plastic cap 28. The diameter of the bore at the proximal end of the cap is such that the bore securely accommodates the distal end of the cannula guide tube 22. The bore increases in diameter in the distal direction to form a bore of greater diameter at 30a. The bore then widens along a conical segment 30b before reassuming a cylindrical shape at 30c, which defines the distal entrance 29 to the bore (and hence to the guide tube) at the distal face 27. An annular ring 24 is affixed to the cannula guide tube 22 intermediate its ends. The outer diameter of the annular ring is less than the inner diameter of the guide housing bore 18 as shown in FIG. 1. A compression spring 32 is located in the cylindrical space between the bore 18 and the cannula guide tube 22. The spring is axially bound by the shoulder 19 of the guide housing 12 and the annular ring 24 affixed to the cannula guide tube 22. The cannula guide tube 22 is axially shiftable within the bore 18 against the spring 32, which urges the cannula guide subassembly 20 to assume the position shown in FIG. 1, in which the proximal face 25 of the cannula cap 28 abuts the distal surface 13 of the guide housing 12.

Once the clinician has made a small incision to mark the site at which the marker is to be placed, the guide assembly is located over the incision. Were one to place the hollow guide tube onto the incision site and press down firmly on the housing, tissue would tend to enter the guide tube, and thereby obstruct its interior. An obturator assembly 40 is provided to prevent this from occurring.

Figure 3:
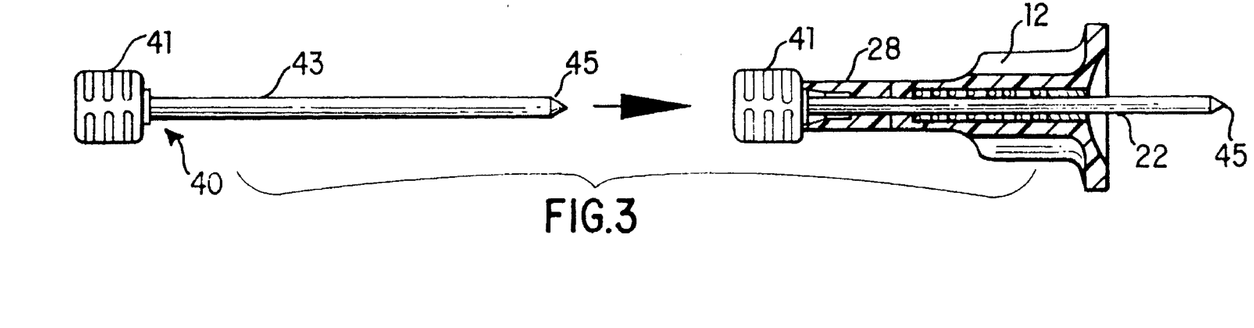
FIG. 3 shows the obturator and its engagement with the guide assembly.
Figures 12A, 12B, 12C:
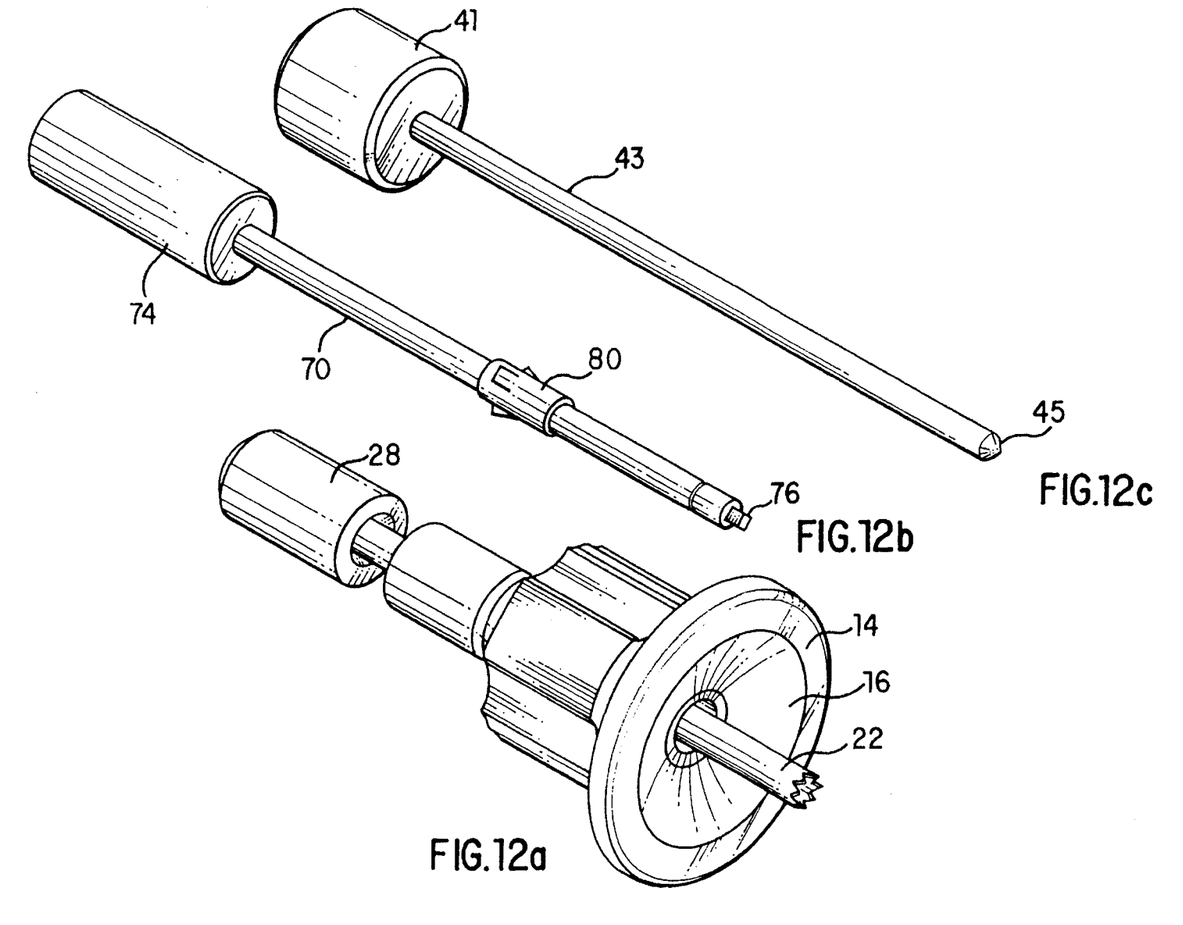
FIGS. 12A–12C provide perspective views of the principal elements of the tool kit, including the guide assembly (FIG. 12A), insertion tool (FIG. 12B) and obturator (FIG. 12C)

With reference to FIGS. 3 and 12C, the obturator assembly 40 of the present invention, which may be made of a plastic material, includes a handle 41 and an obturator shaft 43. The diameter of the shaft 43 is only slightly smaller than the diameter of the bore of the cannula guide tube 22, so that the former can be snugly shifted within the latter without any significant gap between the two. The distal end of the shaft 43 is affixed to the handle 41. A tip 45 is provided at the proximal end of the obturator shaft 43. The obturator shaft 43 is free to move within the cannula guide tube 22 up to the point at which the handle 41 abuts the distal surface 27 of the cannula cap 28.

FIG. 3 illustrates the initial position of the obturator assembly 40 and cannula guide tube subassembly 20 within the guide assembly. Initially, the spring 32 urges the proximal face 25 of the cannula cap 28 on the guide subassembly 20 to abut the distal surface 13 of the guide housing 12. The obturator shaft 43 of the obturator assembly is then inserted into the opening 29 leading to the cannula guide tube 22 until the handle 41 of the obturator abuts the distal face 27 of the guide sub-assembly 20. The obturator is longer than the guide tube, so that its sharp pointed tip 45 protrudes from beyond the sharp teeth 26 at the end of the cannula 22. The clinician touches the obturator tip 45 to the center of the incision, and then orients the guide assembly 10 so that it is orthogonal to the site.

Figure 4:
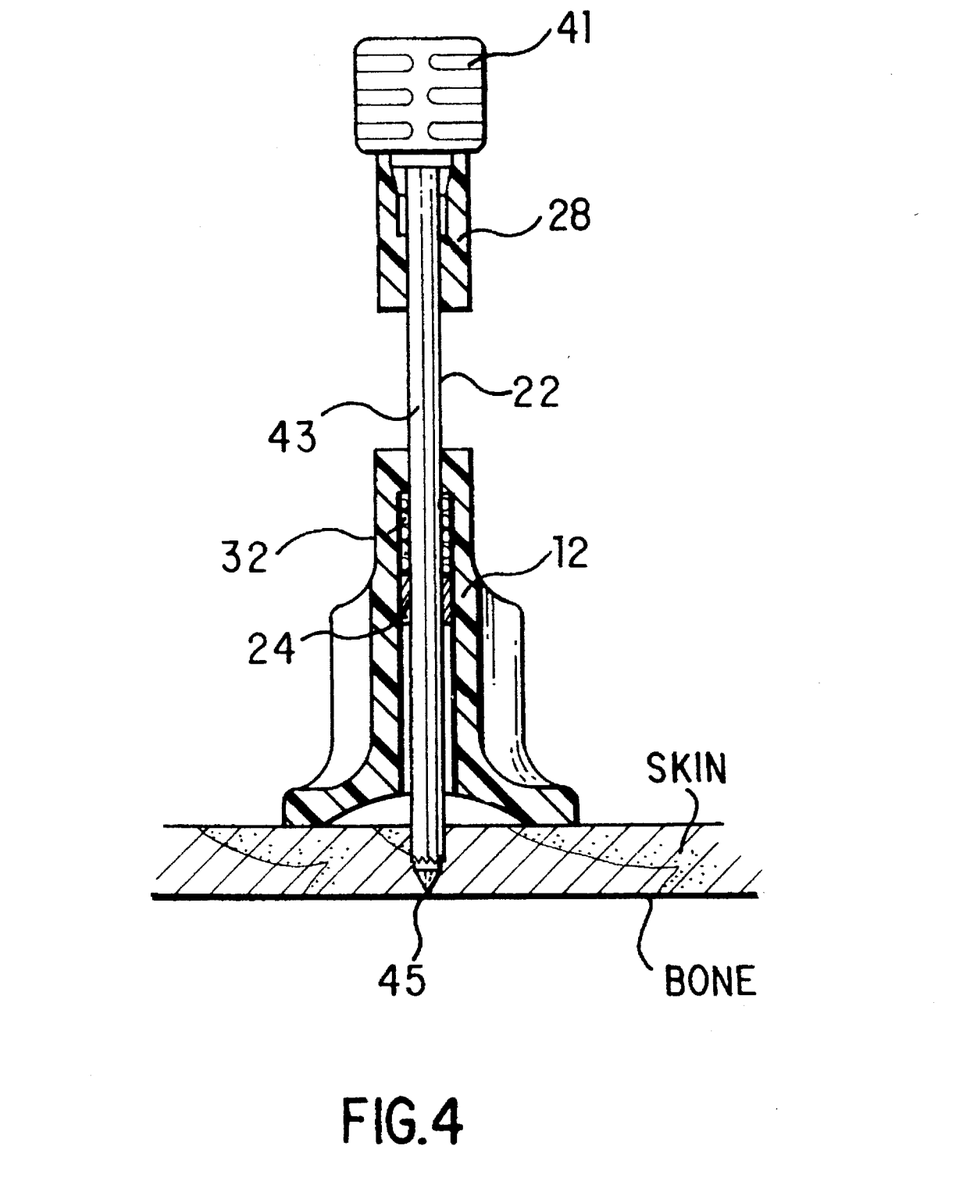
FIG. 4 shows the position of the guide assembly and obturator when the obturator is sited over the insertion site.

The cannula guide tube 22 and housing 12 are manually shifted downward along obturator shaft 43 until the metal cannula guide tube 22 contacts the implantation site. The housing is then downwardly shifted along the cannula guide tube 22 until the flange-like base 14 of the housing makes contact with the skin of the patient along the periphery of the base 14 (see FIG. 4). At this stage, the obturator assembly is removed. The downward movement of the housing along the cannula guide tube 22 causes the spring 32 to undergo compression, which generates a force that is transmitted through the cannula guide tube 22 to the implantation site. Hence, the shifting of the housing generates a force that serves to secure the cannula to the implantation site. The force necessary to compress the spring is provided by the clinician, who must maintain a force against the housing in order to counter the natural tendency of the spring to return to its initial state and thereby cause the housing to shift away from the patient. The combination of forces provided by the spring and the clinician, and the provision of a broad, flange-like base 14 and a sharp-toothed cannula guide tube 22 through which these forces are transmitted to and from the patient, provide a firm and stable connection between the guide assembly and the patient.

Figure 6:
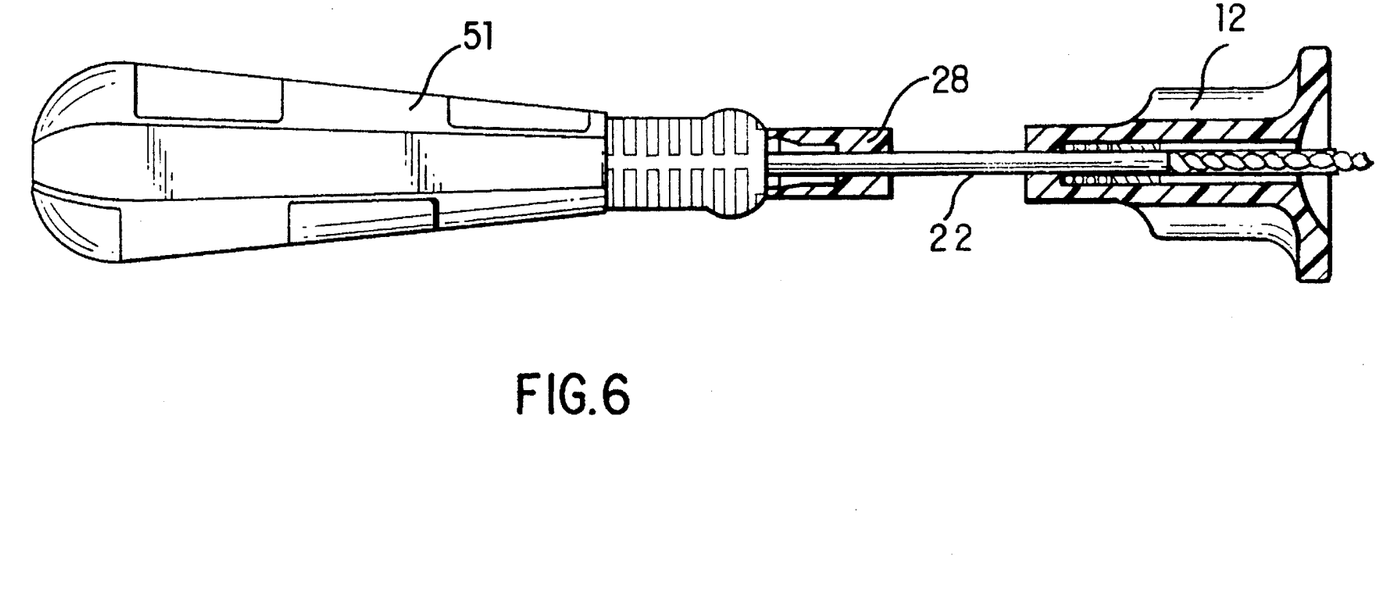
FIG. 6 is a side view, partially in section, of the hand drill inserted in the guide assembly.

After the housing and guide assembly have been positioned, a drill means is inserted into the cannula guide tube 22, as shown in FIG. 6. The hole depth desired is determined by the requirements of the marker one wishes to implant. For example, in the case of a permanent marker, the hole depth is generally equal to the over-all height of the marker. Where the apparatus is to be used to implant a temporary marker base, the hole depth may be equal to the length of the threaded portion of the marker base employed.

FIGS. 5A–5E illustrate one embodiment of a drill means of the present invention, in which the drill means is a hand drill 50 having a handle 51 to which is attached a drill bit 52. (It is within the scope of this invention to employ a power drill in place of a hand drill.) The drill bit 52 may either be permanently fixed to the handle, or, preferably, it may be readily removable therefrom for replacement by other drill bits. The drill bit 52 has a diameter that is slightly smaller than the inner bore diameter of the cannula guide tube 22, and is shiftable within the guide tube 22. In one embodiment, the axial movement of the drill 50 within the guide tube is limited by the abutment provided by a shoulder 54 on the proximal end of the hand drill with respect to the distal surface 27 of cannula guide tube 22. This abutment serves to limit the depth of the hole that can be made. Conventional spacer rings (not shown) placed about the shaft of the drill bit in abutting relationship with the handle shoulder 54 can be used to further limit the depth of hole which can be made with a given drill bit.

Figure 5A:
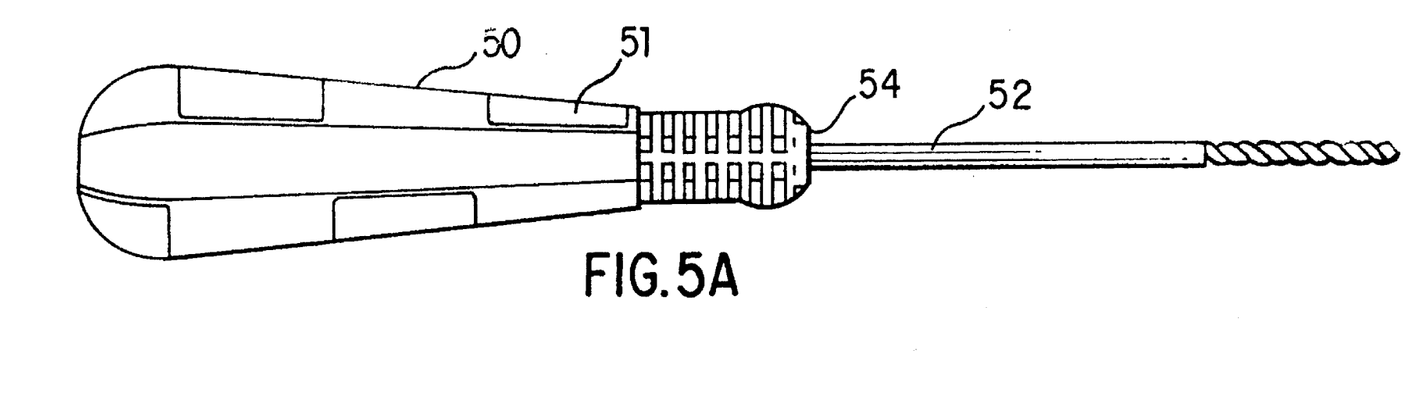
FIG. 5A is a plan view of the hand drill.
Figure 5B:
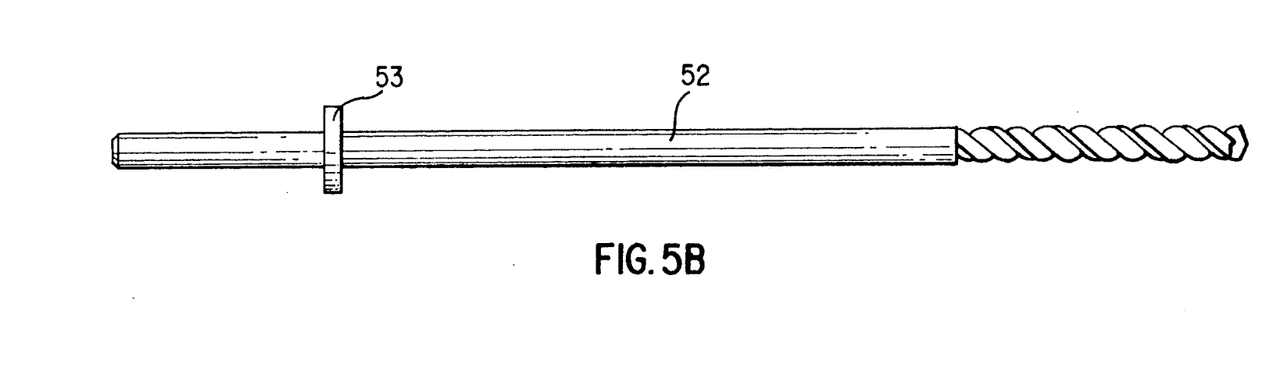
FIGS. 5B and 5C are side and end views, respectively, of a drill bit employed with the hand drill.
Figure 5C:
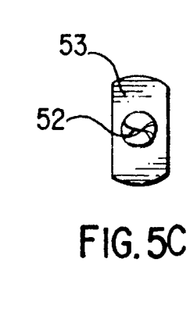
Figure 5D:
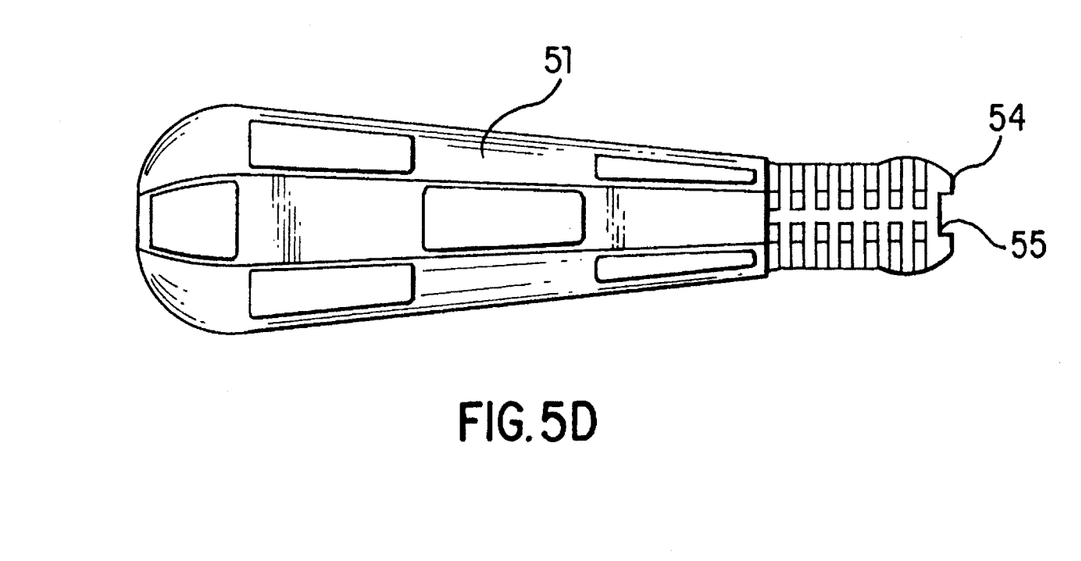
FIGS. 5D and 5E are side and end views, respectively, of the handle portion of the hand drill.
Figure 5E:
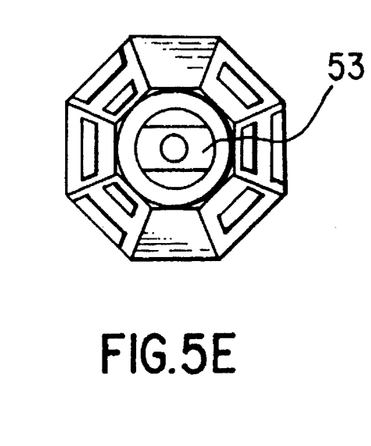

In the preferred embodiment shown in FIGS. 5B and 5C, the abutment is provided by a shoulder 53 mounted to the drill bit 52. In addition to including a bore to accommodate the distal end of the drill bit, the handle 51 also may have a slot 55 at its proximal end to accommodate the shoulder 53. As with the other embodiments, the shoulder 53 abuts the distal surface 27 of the guide tube to limit the further axial movement of the drill bit.

After the drill bit has been inserted into the cannula to the point at which it makes contact with tissue, its handle 51 is rotated within the guide tube 22, which causes the drill bit 52 to penetrate and bore a hole in the bone. Because of the abutment provided between the drill bit shoulder 53, handle shoulder 54, or spacer washers with the distal face 27 of the guide tube, the depth of hole that is drilled is determined by the degree to which the drill bit protrudes from the guide tube 22 once the depth-limiting abutment has been reached (see FIG. 6).

Figure 7A:
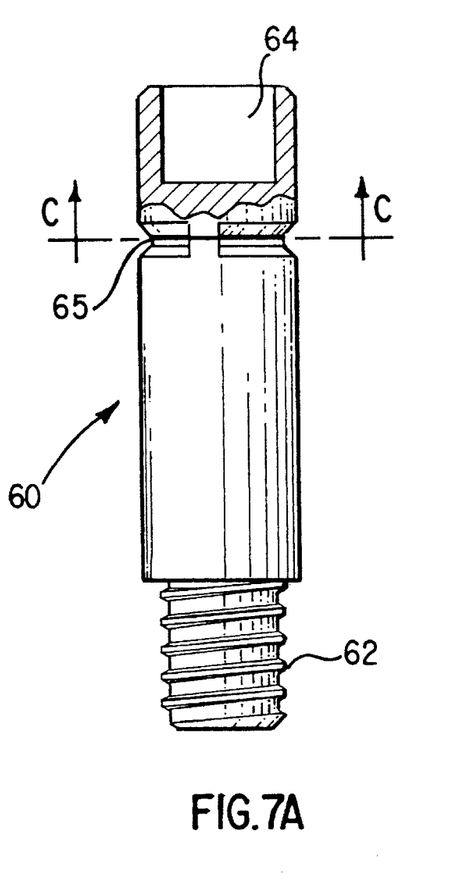
FIG. 7A shows a temporary marker base that can be used with the present invention.
Figure 7B:
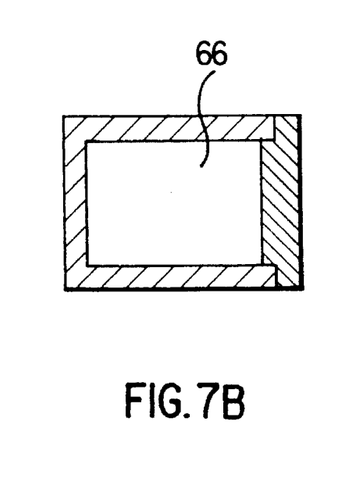
FIG. 7B shows a permanent marker that can be used with the present invention.
Figure 8:
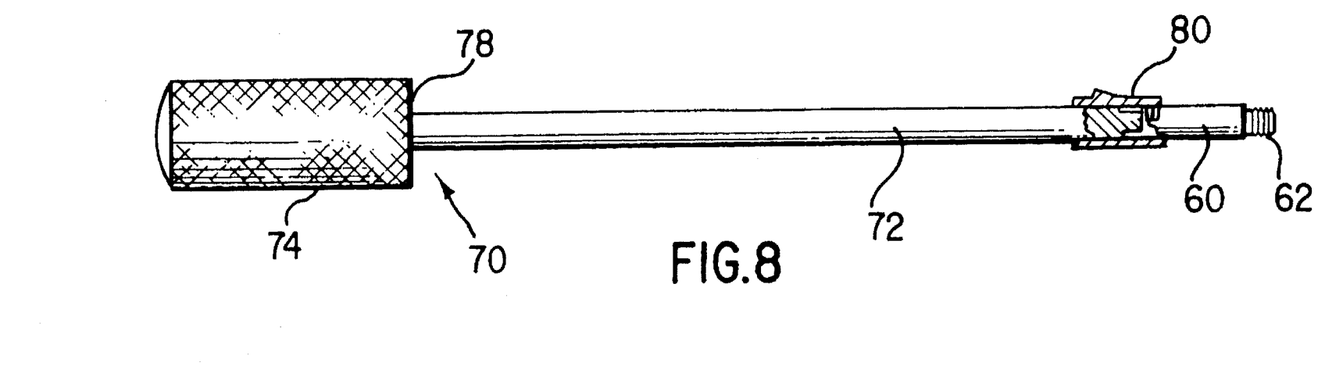
FIG. 8 is a side view, partially in section, of the cooperation between the insertion tool, clip, and temporary marker base.
Figure 9A:
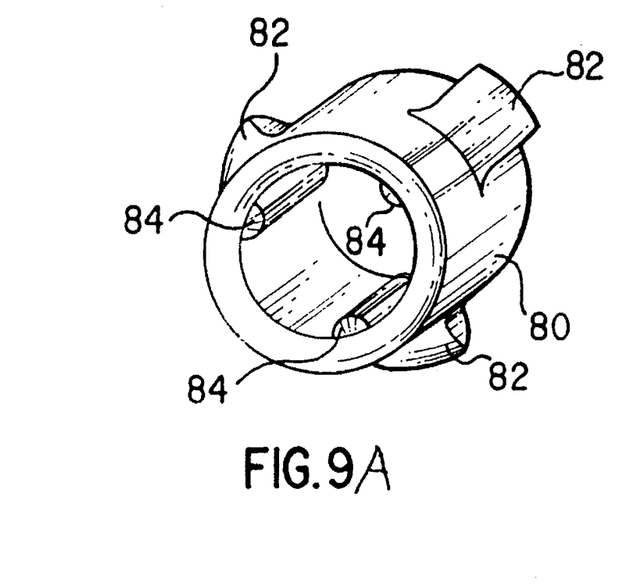
FIG. 9A is a perspective view of the clip shown in FIG. 8, which helps secure the temporary marker base to the insertion tool.
Figure 9B:
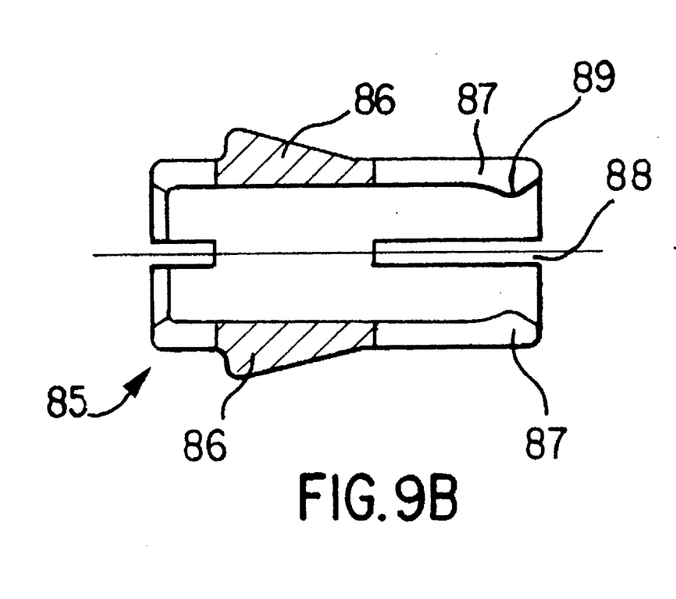
FIG. 9B is a side-sectional view of a clip which is configured to secure a permanent marker to the insertion tool.
Figure 9C:
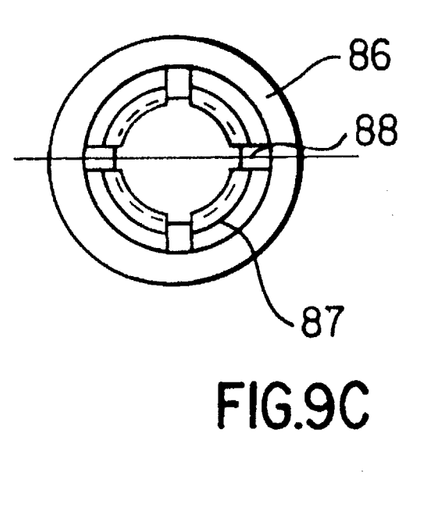
FIG. 9C is an end view of the clip shown in FIG. 9B.

Once the hole has been drilled, the drill is removed from the guide tube. A marker insertion tool 70 is employed to insert the permanent marker or temporary marker base 60. The insertion tool 70, which may be made of stainless steel, consists of a shaft 72 that is joined at its distal end to a knurled handle 74 (see FIGS. 8 and 12B). The diameter of the shaft 72 is slightly smaller than the inner diameter of the cannula guide tube 22 so as to be shiftable therein. At its proximal end, the metal shaft terminates in a driver tip 76, which may take the form of a boss. FIG. 7B illustrates a permanent fiducial marker 66. The permanent marker has the general shape of a cylinder, and can be inserted merely by inserting the marker and proximal end of the insertion tool into the cannula guide tube 22 and then pressing down on the distal surface of the marker with the tip of the insertion tool until it is securely placed within the hole that has been drilled for it. However, the process can be facilitated by first providing a means for detachably securing the permanent marker to the shaft of the insertion tool 70. Such a means is provided by a clip 85. As shown in FIGS. 9B and 9C, the clip is a generally cylindrical body that is sufficiently long to accommodate the permanent marker 66, as well as the proximal tip of the insertion tool shaft 72. The outer surface of the marker includes an annular conical portion 86 that is configured to mate with conical segment 30b of the cannula cap 28. Properly sited on the shaft 72, the clip 85 straddles the shaft, protruding beyond it a distance sufficient to securely accommodate the marker 66 behind a series of four prongs 87, each separated from its neighboring prong by a slot 88. The prongs terminate in inwardly directed protrusions 89 that prevent the marker from falling out of the clip 85. After the marker and clip have been mounted to the tip of the insertion tool, the clip is placed into the cap 28. The annular conical surface 86 of the clip 85 then abuts against the conical segment 30b of the cannula guide tube cap 28 as the shaft is inserted into the guide housing. Further movement of the shaft causes the prongs of the clip (which is constructed of plastic) to flare outwardly to an extent sufficient to permit the marker to move past the prong protrusions 89 and so enter the cannula guide tube 22. The implantation of a temporary fiducial marker will generally involve the implantation of a marker base, such as is shown in FIG. 7A. This marker base has self tapping threads 62, and must be screwed into the hole; it is, therefore, necessary to provide a drive connection at the driver tip 76 between the insertion tool and the marker base. This is provided by a boss at the driver tip 76, which is sized and shaped to cooperate with a corresponding socket 64 on the marker base 60. The marker base 60 is connected to the insertion tool at the driver tip, and then inserted along with the proximal end of the insertion tool into the cannula. The insertion tool is pushed into the cannula until the threaded portion 62 of the marker base begins to contact bone. Once contact is made, the handle 74 of the insertion tool is rotated, and the marker base (whose threads are self-tapping) is screwed into the hole formed by the drill. Insertion is completed when the proximal end 78 of the insertion tool makes contact with the distal surface 27 of the cannula cap 28. The procedure is then complete, and the guide assembly and the insertion tool are then removed from the site. At this point, the clinician can attache the imaging marker to the marker base, as is further set forth in co-pending application Ser. No. 08/017,167.

Figure 10:
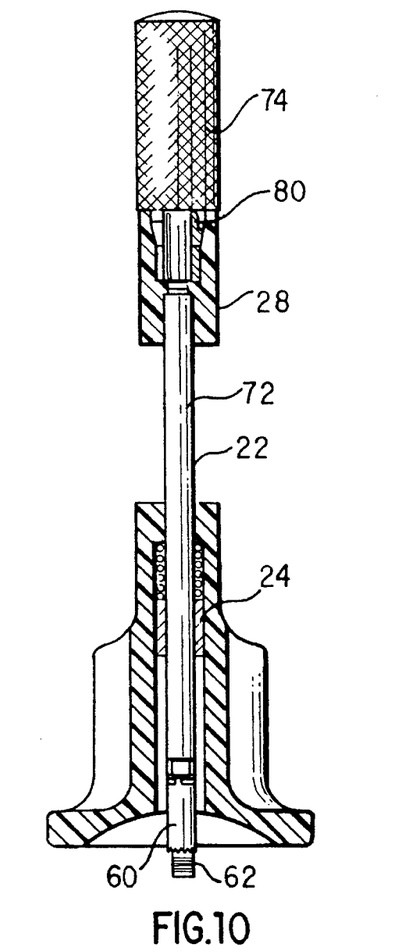
FIG. 10 is a sectional view showing the insertion tool, the temporary marker base and guide housing, in which the cannula guide tube is shown shifted with respect to the guide housing.
Figure 11:
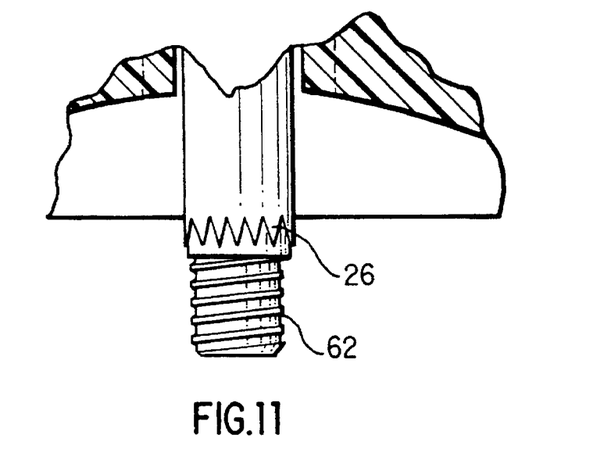
FIG. 11 is a magnified view of the proximal end of FIG. 10, and highlights the tip of the proximal end of the cannula and the threaded portion of the temporary marker base.

As with the permanent marker, a clip 80 can be provided to better secure the temporary marker base to the shaft 72 prior to the insertion of the marker base into cannula. The clip 80 is an annularly shaped plastic element that is sized to fit over and grip the shaft 72 of the insertion tool (see FIG. 9A). As is shown in FIG. 8, the clip is placed so that a portion of its axial length protrudes from beyond the proximal tip of the drive shaft 72. The marker base or marker is then inserted into this protruding length of the clip, which has a series of nubs 84 that cooperate with a groove 65 on the temporary marker base so as to provide a secure, though detachable, connection between the clip and base. Upon insertion of the marker base into the cannula, a series of three protrusions 82 (see FIG. 9A) engage and seat against the conical surface 30B of the cannula cap 28. Further insertion of the drive tool causes the clip, which is too large to move beyond this point, to release the temporary marker base, freeing it to move with the tip of the shaft 72 past the now seated clip through the cannula guide tube 22 towards the hole, where it is screwed into place (see FIGS. 10 and 11).

Removal of the marker base is a simple matter. The insertion tool can be used to rotate the marker base in the opposite direction so as to remove the marker base from the bone.

Figure 13A:
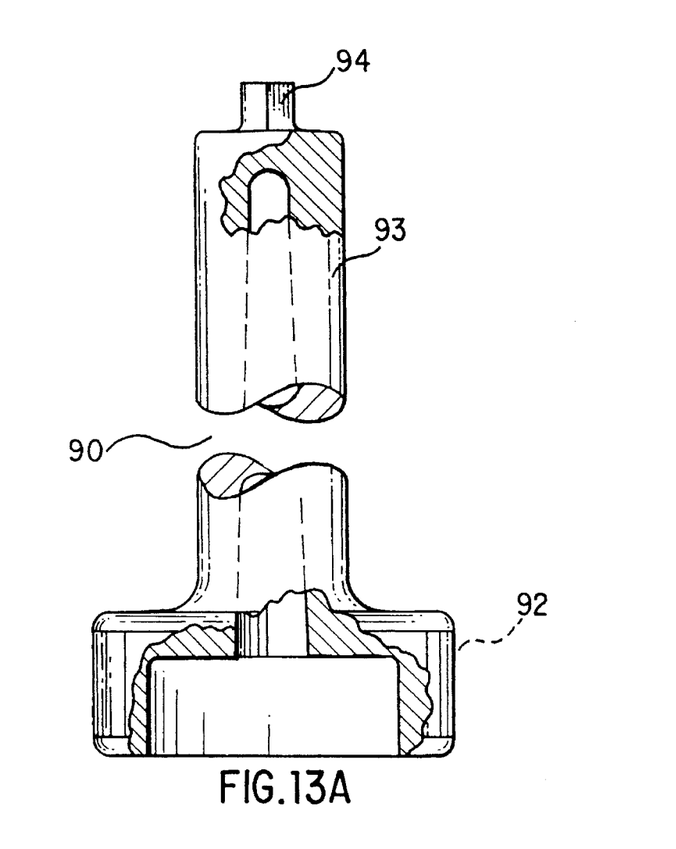
FIGS. 13A and 13B are partial side sectional and end views, respectively, of a tool for removing the base of a temporary fiducial marker after it has been inserted.
Figure 13B:
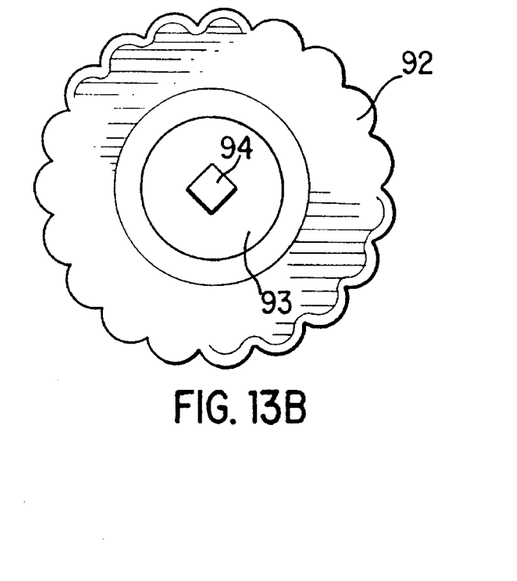

In a preferred embodiment, a specialized removal tool is used (see FIGS. 13A and 13B). The removal tool 90 consists of a knob 92 attached to a shaft 92 that terminates in a boss 94. The boss 94 is sized to mate with the socket 64 on the temporary marker base. In order to remove the marker base, one inserts the boss 94 into the socket 64 and turns the knob 92 until the marker base is unscrewed from its hole.

Figure 14A:
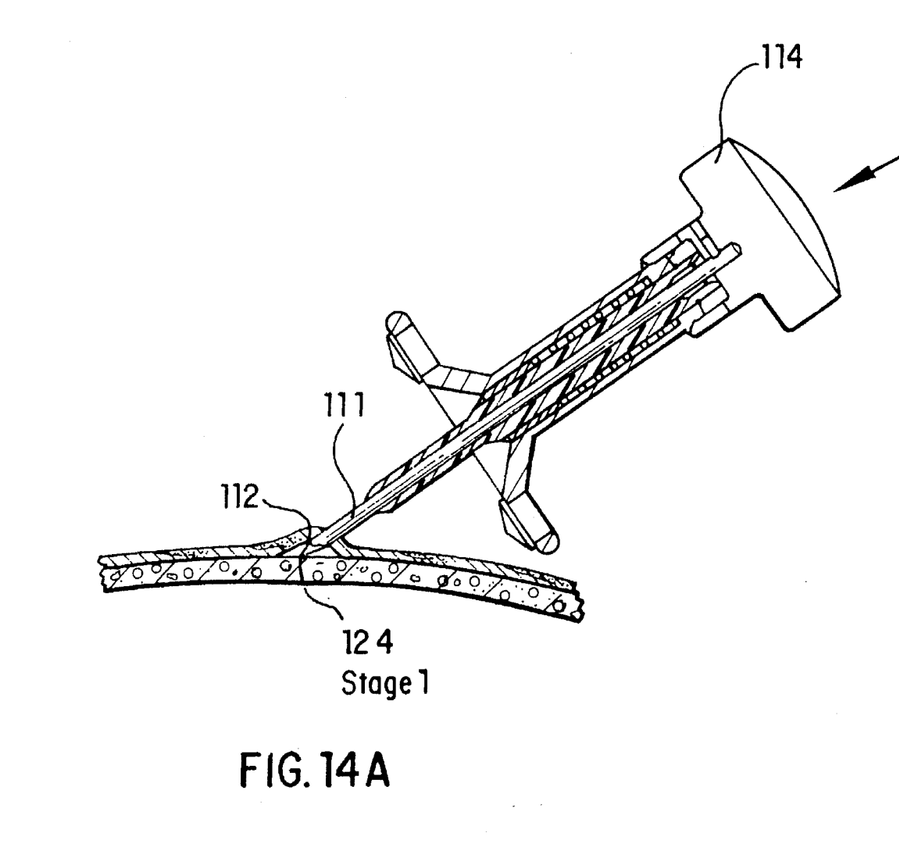
FIG. 14A is a sectional view of the embodiment at a first stage of its use and FIG. 14B is an elevational view of the embodiment at a second stage of its use.
Figure 14B:
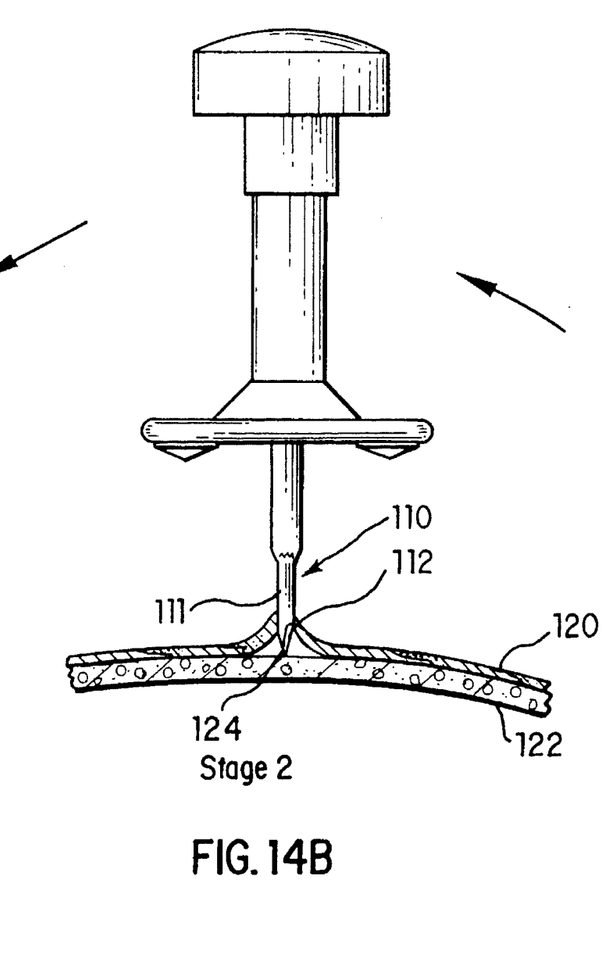

FIGS. 14A and 14B illustrate a further embodiment of the invention, differing from the previous embodiment chiefly in that a trocar 110 is employed initially to site the apparatus instead of an obturator. The trocar 110 is composed of a stainless steel shaft 111 attached to a handle 114. The opposite end of the trocar terminates in sharp pointed end 112.

In use, the trocar is first inserted into the cannula of the guide assembly. (While the guide assembly shown in FIGS. 14A and 14B is somewhat different from that shown in the previous Figures, it should be understood that the trocar can be employed with the housing shown in the previous figures as well.) Whereas in the previous embodiment, the surgeon marks the location at which the marker or marker base are to be inserted with a small incision in the skin made with a scalpel, in this embodiment the tip of the trocar is used to pierce the skin 120. This penetration is done at an angle as shown in FIG. 14A (stage 1) so that the point at which the skin 120 is penetrated does not lie directly over the point at which the tip 112 makes contact with the underlying bone 122, which is the implantation site 124. Then, as shown in FIG. 14B (stage 2), the trocar and housing are pivoted about the point of contact between the trocar tip 112 and the bone (i.e., the implantation site 124) until the housing and trocar are perpendicular with respect to the bone. The housing (including the cannula) is then shifted down along the trocar, which is then removed. The remainder of the procedure is the same as that which has been discussed above with respect to the previous embodiment employing an obturator.

The advantage of separating the point at which the skin is penetrated by the trocar (and through which the drill and insertion tool then pass) from the point of the skin which, when the skin is not stretched, actually overlies the location on the bone at which the hole is to be drilled, is that it provides a natural skin covering over the implantation site, which helps reduce the risk of infection.

What is claimed is:

1. An apparatus for inserting a fiducial marker component into a patient, comprising:

a housing that is generally cylindrically shaped and which has a bore provided therein, said housing having a proximal end and a distal end, at least a portion of the proximal end of the housing flaring outward from the body of the housing so as to provide an area for stably supporting the housing against a surface on a patient;

a cannula guide tube assembly that has a proximal end and a distal end and which contains a bore;

a drill for forming a bore hole at an implantation site; and an inserter for inserting a fiducial marker component in the bore hole at the implantation site;

wherein the cannula guide tube is shiftable within said bore of said housing and the drill and inserter are each separately insertable into said guide tube and shiftable therein.

2. The apparatus for inserting a fiducial marker component according to claim 1, wherein the housing has a longitudinal axis and wherein the portion of the cylindrical housing that flares outward forms a flange at the housing than extends in a perpendicular direction away from the longitudinal axis of the housing.

3. The apparatus for inserting a fiducial marker component according to claim 1, wherein said guide tube is provided with teeth.

4. The apparatus for inserting a fiducial marker component according to claim 1, wherein said guide tube has an outer surface on which is provided at least one abutment surface near said distal end of the guide tube to contact the housing and thereby limit movement of the guide tube with respect to the housing.

5. The apparatus for inserting a fiducial marker component according to claim 1, further comprising a spring disposed within the bore of said housing such that said guide tube fits within said housing and is shiftable therein against a force provided by said spring.

6. The apparatus nor inserting a fiducial marker component according to claim 1, further comprising an obturator assembly that is separately insertable into the guide tube and shiftable therein separately from the drill and the inserter.

7. The apparatus for inserting a fiducial marker component according to claim 6, wherein said obturator assembly further comprises a handle and an obturator shaft that has a smaller diameter than the bore of the guide tube, wherein the obturator shaft is affixed to said handle.

8. The apparatus for inserting a fiducial marker component according to claim 1, wherein said drill comprises a handle and a drill bit having a smaller diameter than the bore of the guide tube, said drill bit being disposed in said handle.

9. The apparatus for inserting a fiducial marker component according to claim 1, wherein said inserter comprises a driver shaft and a handle to which the driver shaft is attached, wherein the diameter of the shaft is smaller than the diameter of the housing bore.

10. The apparatus of claim 9, further comprising a cylindrically-shaped clip that is sized to grip the shaft of the driver.

11. The apparatus for inserting a fiducial marker component according to claim 1, further comprising a trocar assembly that is insertable into the guide tube and shiftable therein.

12. The apparatus for inserting a fiducial marker component according to claim 11, wherein said trocar assembly further comprises a handle and an trocar shaft that has a smaller diameter than said guide tube bore, one end of said trocar shaft terminating in a sharp point and wherein the other end of the trocar shaft is affixed to said handle.

13. An apparatus for inserting a fiducial marker component, comprising:

a housing defining an axially disposed bore, wherein the diameter of the bore is stepped so as to define a shoulder, said housing having a proximal end and a distal end, at least a portion of the proximal end extending laterally away from the bore so as to provide an area for stably supporting the housing against a surface;

a cannula, said cannula having a proximal end, a distal end, an exterior surface and a shoulder attached to the exterior surface of the cannula between the proximal and distal ends of the cannula; and a spring located within the bore of the housing and bound at its ends by the bore shoulder and the cannula shoulder, wherein the cannula is freely shiftable within the bore so as to limit the length of the spring.

14. The apparatus for inserting a fiducial marker component of claim 13, further comprising an insertion tool that is separately insertable into the cannula and shiftable therein, said insertion tool comprising a metal shaft.

15. The apparatus for inserting a fiducial marker component of claim 14, wherein the insertion tool further includes a clip for affixing a cylindrical object to the terminus of the shaft.

16. The apparatus for inserting a fiducial marker component of claim 14, wherein the insertion tool includes a handle at one end of the shaft and a drive element at the tip of the other end of the shaft.

17. The apparatus for inserting a fiducial marker component of claim 13, further comprising a drill having a shaft that is insertable into the cannula and shiftable therein.

18. The apparatus of claim 17, wherein the drill is a hand drill.

19. The apparatus of claim 17, wherein the drill is a power drill.

20. The apparatus for inserting a fiducial marker component of claim 18, wherein the cannula has an upper external surface that defines an abutment surface, the drill has a facing abutment surface, and wherein the drill can be inserted into the cannula up to the point at which the abutment surface of the drill contacts the abutment surface of the cannula, thereby limiting the depth of hole that can be made by the drill.

21. The apparatus for inserting a fiducial marker component of claim 13, wherein the housing has an annular flange at one of its ends.

22. The apparatus for inserting a fiducial marker component of claim 13, wherein the cannula has means for gripping an underlying surface at one of its ends.

23. The apparatus for inserting a fiducial marker component of claim 13, wherein the cannula is affixed to a knob containing a bore.

24. The apparatus for inserting a fiducial marker component of claim 23, further comprising a clip having attachment means to affix a fiducial marker component with respect to the terminal portion of the shaft of an insertion tool, and wherein the bore in the knob of the cannula includes a seat for the clip.

25. The apparatus for inserting a fiducial marker component of claim 24, wherein the clip comprises:

a cylindrical portion defining a bore; and means distributed along the outer circumference of the clip for seating with the bore in the knob of the cannula.

26. The apparatus for inserting a fiducial marker component of claim 25, wherein the cylindrical portion of the clip further includes a plurality of inwardly directed prongs that are elastically displaceable with respect to each other.

27. The apparatus for inserting a fiducial marker component of claim 26, wherein the prongs of the clip terminate in an inwardly directed projection.

28. The apparatus for inserting a fiducial marker component of claim 25, wherein a series of inwardly directed hubs are circumferentially arrayed along the interior of the cylindrical portion of the clip.

29. The apparatus for inserting a fiducial marker component of claim 13, wherein the housing is made of plastic.

30. The apparatus for inserting a fiducial marker component of claim 13, wherein the cannula is made of metal.

31. The apparatus for inserting a fiducial marker component of claim 13, further including a fiducial marker component comprising a fiducial marker base that is adapted to be inserted through the cannula.

32. The apparatus for inserting a fiducial marker component of claim 31, wherein the fiducial marker base has self tapping threads.

33. The apparatus for inserting a fiducial marker component of claim 13, further including a fiducial marker component comprising a fully implantable fiducial marker that is adapted to be inserted through the cannula.

34. The apparatus for inserting a fiducial marker component of claim 13, wherein the cannula shoulder is in the form of a ring.

35. A tool kit for facilitating the insertion of a cylindrical object into a hole in a portion of anatomy of a patient, comprising:

a housing having two ends, one of which extends from the housing an amount sufficient to provide an area for stably supporting the housing against a surface on the patient;

a spring-loaded cannula that is shiftable within the housing;

a drill for forming a hole, said drill being shiftable within the cannula; and an insertion tool for driving a cylindrical object into the hole formed by the drill.

36. The tool kit of claim 35, further comprising an obturator that is separately shiftable within the cannula.

37. The tool kit of claim 35, further comprising a trocar that is separately shiftable within the cannula.

38. The tool kit of claim 35, further comprising a tool for removing the cylindrical object from the hole.

39. The tool kit of claim 35, further including a cylindrical object comprising a fiducial marker.

40. The tool kit of claim 35, further including a cylindrical object comprising a temporary marker base.

* * * * *